United States Patent

Murakami et al.

[11] 4,127,675
[45] Nov. 28, 1978

[54] 4-(ALKYLAMINO-2-HYDROXYPROPOXY)-INDENES AND METHOD OF USE

[75] Inventors: Masuo Murakami; Kiyoshi Murase; Kunihiro Niigata, all of Tokyo; Shiro Tachikawa, Omiya; Toichi Takenaka, Ageo, all of Japan

[73] Assignee: Yamanouchi Pharmaceutical Co., Ltd., Tokyo, Japan

[21] Appl. No.: 734,514

[22] Filed: Oct. 21, 1976

Related U.S. Application Data

[60] Division of Ser. No. 568,097, Apr. 14, 1975, Pat. No. 4,045,482, which is a continuation of Ser. No. 141,936, May 10, 1971, abandoned, which is a continuation-in-part of Ser. No. 876,070, Nov. 12, 1969, abandoned.

[30] Foreign Application Priority Data

Nov. 12, 1968 [JP] Japan .................................. 43-82297
Sep. 11, 1969 [JP] Japan .................................. 44-72582

[51] Int. Cl.$^2$ .................... C07C 93/06; A61K 31/135
[52] U.S. Cl. .............................. 424/330; 260/348.63; 260/501.18; 260/570 R; 260/570.7; 424/316

[58] Field of Search .................. 260/501.18, 501.19, 260/570.7; 424/316, 330

[56] References Cited

U.S. PATENT DOCUMENTS

| | | | |
|---|---|---|---|
| 3,051,709 | 8/1962 | Shapiro et al. | 260/570.7 X |
| 3,234,211 | 2/1966 | Huebner et al. | 260/570.7 X |
| 3,415,873 | 12/1968 | Stevens | 260/501.18 |

Primary Examiner—Robert V. Hines
Attorney, Agent, or Firm—Wenderoth, Lind & Ponack

[57] ABSTRACT

Novel indene derivatives represented by the general formula

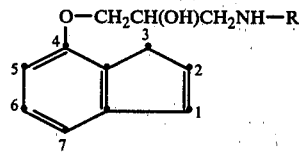

wherein R represents lower alkyl, phenylloweralkyl or lower cycloalkyl, and acid addition salts thereof useful as β-receptor antagonists.

7 Claims, No Drawings

4-(ALKYLAMINO-2-HYDROXYPROPOXY)-INDENES AND METHOD OF USE

This application is a divisional of Ser. No. 568,097, filed Apr. 14, 1975, now U.S. Pat. No. 4,045,482 which is a continuation of Ser. No. 141,936, filed May 10, 1971, now abandoned, which is a continuation-in-part of Ser. No. 876,070, filed Nov. 12, 1969, now abandoned.

This invention relates to novel indene derivatives having valuable therapeutic properties, non-toxic salts thereof, and to processes for their production.

The therapeutically active compounds of this invention are represented by the general formula

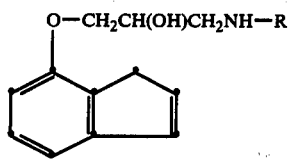

O—CH$_2$CH(OH)CH$_2$NH—R    (I)

wherein R represents a lower alkyl, phenylloweralkyl or lower cycloalkyl group.

The term "lower alkyl" as used herein means both straight and branched chain aliphatic hydrocarbon groups such as methyl, ethyl, propyl, isopropyl, butyl, isobutyl, t-butyl, amyl, hexyl, etc. The term "phenyl-loweralkyl", which may contain more than one phenyl group, is represented by groups such as benzyl, diphenylmethyl, β-phenylisopropyl, etc. The term "lower cycloalkyl" is represented by groups such as cyclopentyl and cyclohexyl, etc.

The compounds I of the present invention can be prepared by reacting a compound of the general formula

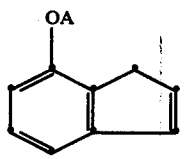

OA    (II)

wherein A represents a hydrogen atom or a 2,3-epoxypropyl group with an amine of the general formula

B—NH—R    (III)

wherein R is defined as above and B represents a 3-halogeno-2-hydroxypropyl group when A is a hydrogen atom; and when A is a 2,3-epoxypropyl group, B is a hydrogen atom.

Thus, according to one embodiment of the process of this invention, the novel compounds I are prepared by condensing a 4-hydroxyindene represented by the formula

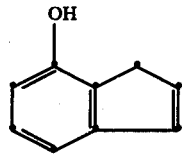

OH    (IV)

with a 1-halogeno-2-hydroxy-3-loweralkylaminopropane of the general formula

X—CH$_2$CH(OH)CH$_2$NH—R    (V)

wherein X represents a halogen atom and R is defined as above.

The reaction is preferably carried out in the presence of an acid-binding agent, preferably an alkali metal or derivative thereof, e.g. a hydroxide, a hydride, an amide, an alcoholate or a metal-alkyl compound.

The reaction is also preferably carried out in the presence of an inert solvent, such as water, methanol, ethanol and the like, at room temperature or at an elevated temperature, e.g. up to the reflux temperature of the solvent.

The novel compounds I of this invention can also be obtained by the condensation of 4-(2,3-epoxypropoxy)indene of the structural formula

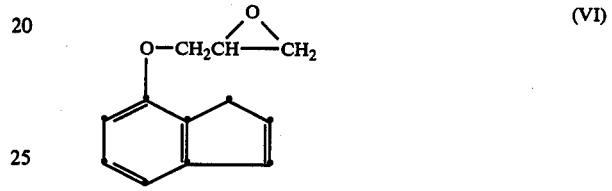

(VI)

with a lower alkyl amine of the general formula

H$_2$N—R    (VII)

wherein R is defined as above.

The reaction of this latter method is carried out in the presence or absence of a suitable inert organic solvent, for example, methanol, ethanol, ether, ethyl acetate and the like at room temperature or at an elevated temperature, e.g. up to the reflux temperature of the solvent.

The 4-(2,3-epoxypropoxy)indene VI employed as a starting material in the above-mentioned process may be prepared by reacting 4-hydroxyindene IV with 1,2-epoxy-3-halogenopropane.

The 4-hydroxyindene IV in solution in a solvent such as water or an organic diluent is isomerized by a basic substance to form 7-hydroxyindene.

Therefore, the compounds I of the present invention contain an isomer, that is 7-(3-loweralkylamino-2-hydroxypropoxy)indene represented by the general formula

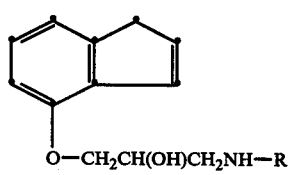

O—CH$_2$CH(OH)CH$_2$NH—R wherein R is as defined above.

The novel compounds I of this invention, of course, contain an asymmetric carbon atom at the 2-position in its side chain and can exist as a d- or l-isomer or a racemate.

From the compounds I of this invention, the substantially non-toxic, i.e. pharmaceutically acceptable, acid addition salts can be prepared in the usual manner with pharmaceutically non-toxic inorganic or organic acids, such as hydrochloric acid, sulfuric acids, nitric acid, phosphoric acid, formic acid and acetic acid.

The compounds I of this invention possess valuable therapeutic properties which render them useful as adrenergic β-receptor blocking agents. (Experiments 1 and 3)

What should be noted as a distinctly meritorious property of the compounds I of this invention is that they improve the cardiac function, while known adrenergic β-receptor antagonists, such as 4-(3-isopropylamino-2-hydroxypropoxy)indane have deleterious effects on the cardiac function. (Experiment 2)

Accordingly, the products I of this invention are useful as adrenergic β-receptor antagonists which can be administered to patients (humans) without the apprehension of damaging the heart.

The compounds I of the present invention are effective when orally administered. Clinically they may be administered orally at a daily dosage of about 5–15 mg., e.g. 10 mg., of the compounds, optionally in divided portions. They may also be administered intramuscularly or intravenously to provide a total daily dosage of about 2–5 mg., e.g. 4 mg., of the compounds, optionally in divided portions. The compounds I may be administered in combination with a pharmaceutically acceptable carrier, e.g. cellulose, starch or talc, or a combination thereof.

The invention will be described in further detail in the following examples which are presented by way of illustration only and not as limiting the scope of the invention.

EXAMPLE I (a) A mixture of 0.9 g. of 4-hydroxyindene, 2.0 g. of 1,2-epoxy-3-chloropropane, 2.7 g. of potassium carbonate and 15 ml. of acetone was refluxed at about 57° C. for 24 hours. Acetone was removed by vacuum distillation, the residue was washed with 10 ml. of water and then extracted with 20 ml. of ether three times. The ether extract was dried with magnesium sulfate, filtered and subjected to column chromatography using a column (having an inside diameter of about 3 cm. and a height of about 50 cm.) packed with silica gel. The 5th to 7th fractions (volume of one fraction is 50 ml.) recovered from the chromatographic column using chloroform as the effluent were combined together and concentrated to provide 0.6 g. of 4-(2,3-epoxypropoxy)indene.

(b) A mixture of 0.42 g. of 4-(2,3-epoxypropoxy)indene, 1.20 g. of isopropylamine and 20 ml. of methanol was stirred in a flask at room temperature for 2 hours. Methanol and unchanged isopropylamine were removed by vacuum distillation and the residue was recrystallized from a mixture of n-hexane and ether to yield 0.41 g. of 4-(3-isopropylamino-2-hydroxypropoxy)indene having a melting point of 88°–89° C.

(c) To a solution of 0.41 g. of 4-(3-isopropylamino-2-hydroxypropoxy)indene in 80 ml. of absolute ether there was added dropwise a hydrochloric acid-ether mixture at 0° C. with stirring. The precipitates thus formed were recovered by filtration and recrystallized from a mixture of ethanol and ether to provide 0.44 g. of the hydrochloride of 4-(3-isopropylamino-2-hydroxypropoxy)indene. M.P. 147°–148° C.

| Elementary analysis as $C_{15}H_{22}NO_2Cl$: | | | |
|---|---|---|---|
| | C (%) | H (%) | N (%) |
| Calculated: | 63.48 | 7.81 | 4.94 |
| Found | 63.52 | 7.86 | 4.96 |

With respect to adrenergic β-receptor blocking action, 4-(3-isopropylamino-2-hydroxypropoxy)indene obtained in Example 1 and 4-(3-isopropylamino-2-hydroxypropoxy)indane were tested according to Experiment 1.

Experiment 1

The atria obtained from a male Hartley guinea pig weighing 300–500 g. were trimmed and placed in chambers containing Tyrode solution oxygenated with 95% oxygen and 5% carbon dioxide and maintained at 30° C.

Contractile force was recorded by an isometric lever connected to a strain gauge tension transducer. Antagonistic activity of the tested drugs on the 1-isoproterenol-induced increase of the atrial contraction was investigated.

The first control response was measured adding 1-isoproterenol to the bath fluid to a final concentration of $5 \times 10^{-8}$ g./ml. Then the preparation was washed and the same procedure was repeated after application of the drugs to be tested, i.e. 4-(3-isopropylamino-2-hydroxypropoxy)indene and 4-(3-isopropylamino-2-hydroxypropoxy)indane (final concentrations of $8 \times 10^{-9}$ g./ml. and $5 \times 10^{-8}$ g./ml.), 10 minutes previously. The results are indicated in Table 1.

Table 1

| Compound tested | Dose (g./ml.) | Inhibition rate (%) |
|---|---|---|
| 4-(3-isopropylamino-2-hydroxypropoxy) indene | $8 \times 10^{-9}$ $5 \times 10^{-8}$ | 30.7 81.5 |
| 4-(3-isopropylamino-2-hydroxypropoxy)indane | $8 \times 10^{-9}$ $5 \times 10^{-8}$ | 30.4 88.4 |

Direct effects of these same compounds on a heart devoid of autonomous nervous control were investigated according to Experiment 2.

Experiment 2

The studies were performed on Wistar rats weighing 250–350 g. anesthetized with pentobarbital (50 mg./kg., i.p.) 18–24 hours after treatment with reserpine (8 mg./kg., s.c.). Both adrenal glands were removed and bilateral vagotomy in the neck was performed. One ml./kg. of 4-(3-isopropylamino-2-hydroxypropoxy)indene or 4-(3-isopropylamino-2-hydroxypropoxy)indane was injected intravenously over three minutes in a single dose varying from 0.01 to 0.1 mg./kg. and the heart rate was recorded by a cardiotachometer of Nihon Koden Co. (RM 100). The results are indicated in Table 2. In Table 2, the symbol + represents an increase in heart rate, while the symbol − represents a decrease in heart rate. The standard error is shown in parenthesis.

Table 2

| Compound tested | Number of animals | Dose (mg./kg.) | Change of heart rate (%) | | | |
|---|---|---|---|---|---|---|
| | | | 1 minute after | 5 minutes after | 15 minutes after | 30 minutes after |
| 4-(3-iso-propylamino-2-hydroxy- | 2 | 0.01 | +2.4 (±) 0.9 | +3.8 (±0.2) | +3.2 (±0.1) | +1.7 (±0.2) |
| | | | +5.6 | +8.4 | +8.7 | +5.2 |

Table 2-continued

| Compound tested | Number of animals | Dose (mg./kg.) | Change of heart rate (%) | | | |
|---|---|---|---|---|---|---|
| | | | 1 minute after | 5 minutes after | 15 minutes after | 30 minutes after |
| propoxy)-indene | 4 | 0.05 | (±2.1) +1.5 | (±3.4) +4.1 | (±4.0) +3.5 | (±3.1) +4.0 |
| | 3 | 0.10 | (±0.4) −0.9 | (±1.2) +0.3 | (±1.4) −1.9 | (±2.0) −1.7 |
| 4-(3-iso-propylamino-2-hydroxy-propoxy)-indane | 3 | 0.01 | (±0.1) −2.1 | (±0.8) −2.0 | (±0.9) −2.0 | (±0.3) −4.6 |
| | 4 | 0.05 | (±0.5) −5.9 | (±0.5) −8.7 | (±0.9) −8.7 | (±1.4) −5.4 |
| | 2 | 0.10 | (±1.4) | (±0.3) | (35 0.3) | (±0.6) |

When 4-(3-isopropylamino-2-hydroxypropoxy)indene is injected intravenously to white mice, the $LD_{50}$ value is 25 mg./kg.

Experiment 3

The effects of certain compounds on isoproterenol-induced tachycardia as well as on resting heart rate were studied in reserpinized, vagotomized rats. The rat was anaesthetized with pentobarbital 18 hours after treatment with reserpine (8 mg./kg., i.p.) and vagotomized bilaterally in the neck. Heart rate was recorded by a cardiotacho-meter (RT-2, Nihonkoden). After the control response to l-isoproterenol (0.1 μg./kg., i.v.) was obtained, each compound tested was injected intravenously in such doses that the cumulative dose increased four-fold: 0.01–0.04–0.16–0.64–2.56 mg./kg., at 20 minute intervals. Ten minutes after each dose of the compound an intravenous injection of l-isoproterenol (0.1 μg./kg.) was administered and the increase in heart rate was recorded. The dose producing 50% blockade of the positive chronotropic control response to l-isoproterenol (ED-50) was estimated in each experiment from curves obtained by plotting inhibition percentage against log cumulative dose. The results are indicated in Table 3, in which the standard error is provided by the ± designation.

4-(3-isopropylamino-2-hydroxypropoxy)indene was obtained.

When the crystals obtained above were mixed with the 4-(3-isopropylamino-2-hydroxypropoxy)indene obtained according to the process of Example 1, no lowering of melting point was observed.

EXAMPLE III

Preparation of tablets.
Prescription
| 4-(3-isopropylamino-2-hydroxy-propoxy)indene | 0.2 g. |
| Microcrystalline Cellulose | 1.4 g. |
| Starch | 0.7 g. |
| Talc | 0.2 g. |

This mixture was made into 20 tablets. The tablets were formed on a 7.0 mm. deep cup punch. They may be coated according to conventional methods if desired.

EXAMPLE IV

Preparation of Injections

In 100 ml. of saline solution there were dissolved 100 mg. of 4-(3-isopropylamino-2-hydroxypropoxy)indene hydrochloride and the solution thus formed was aseptically divided by 2 ml. into 50 ampoules each containing 2 mg. of the active compound.

Table 3

| Compound tested | Number of animals | | Control | Dose of compound (mg/kg, i.v.) | | | | | ED50 (mg/kg) |
|---|---|---|---|---|---|---|---|---|---|
| | | | | 0.01 | 0.04 | 0.16 | 0.64 | 2.56 | |
| saline | 2 | BHR[a] | 210, 295 | 205, 295 | 210, 290 | 215, 285 | 210, 290 | — | |
| | | Res[b] | 100, 100 | 106  94 | 102, 100 | 108, 105 | 102, 103 | — | — |
| 4-(3-isopropyl-amino-2-hydroxy-propoxy)indene | 6 | BHR | 232±6 | 235±12 | 246±13 | 245±14 | 245±12 | — | |
| | | Res | 100 | 74±3 | 50±2 | 23±2 | 5±1 | — | 0.039±0.002 |
| 4-(3-sec-butyl-amino-2-hydroxy-propoxy)indene | 4 | BHR | 218±6 | 200±13 | 218±13 | 225±14 | 236±16 | 228±23 | |
| | | Res | 100 | 81±4 | 65±1 | 40±5 | 17±3 | 6±1 | 0.088±0.011 |
| 4-(3-isopropyl-amino-2-hydroxy-propoxy)indane | 3 | BHR | 265±15 | | 245±15 | 236±14 | 238±17 | — | |
| | | Res | 100 | | 54±5 | 33±14 | 12±1 | — | 0.065±0.013 |
| propranolol (Inderal) | 4 | BHR | 250±10 | 253±17 | 251±18 | 230±10 | 225±13 | — | |
| | | Res | 100 | 79±4 | 57±4 | 38±7 | 21±3 | — | 0.063±0.009 |
| alprenolol (Aptin) | 4 | BHR | 225±12 | 233±12 | 247±11 | 261±7 | 262±4 | — | |
| | | Res | 100 | 65±3 | 44±3 | 17±3 | 3±1 | — | 0.030±0.003 | abbreviations; [a]BHR : Basic heart rate (the heart rate just before administration of l-isoproterenol, unit = beat per minute)
[b]Res : Response (percent increase of heart rate induced by 0.1 μg/kg l-isoproterenol)

EXAMPLE II

To a solution of 0.44 g. of 4-hydroxyindene in 4 ml. of an aqueous 10% potassium hydroxide solution there was added 0.65 g. of 1-chloro-2-hydroxy-3-isopropylaminopropane. After stirring the resulting mixture at room temperature for 15 hours, the reaction mixture was extracted with ether, the ether extract was dried with anhydrous sodium carbonate and the ether was distilled off under reduced pressure. The residue was subjected to silica gel column chromatography using acetone as eluent, and 0.23 g. of white crystals of

EXAMPLE V

To a solution of 1 g of 4-(2,3-epoxypropoxy)indene in 8 ml. of absolute ethanol was added 1.2 g. of sec-butylamine and the resulting solution was stirred at room temperature overnight. The reaction solution was concentrated under reduced pressure to give a yellow oily product, which was dissolved in 25 ml. of ether. To the resulting solution was added dropwise hydrogen chloride in ether to form white precipitates. The precipitates thus formed were recovered by filtration and recrystallized from isopropyl alcohol to provide 1.1 g. of the hydrochloride of 4-(3-sec-butylamino-2-hydroxypropoxy)indene. M.P. 125°–126° C.

| Elementary analysis as $C_{16}H_{24}NO_2Cl$ | | | | |
|---|---|---|---|---|
|  | C(%) | H(%) | N(%) | Cl(%) |
| Calculated: | 64.53 | 8.12 | 4.70 | 11.90 |
| Found: | 64.30 | 8.12 | 4.83 | 11.72 |

EXAMPLE VI

To a solution of 1 g. of 4-(2,3-epoxypropoxy)indene in 6 ml. of absolute ethanol was added 1.6 g. of cyclohexylamine and the resulting solution was stirred at room temperature overnight. The solution thus obtained was concentrated under reduced pressure to give a yellow oily product, which was dissolved in 25 ml. of ether. To the resulting ether solution was added dropwise hydrogen chloride in ether to form white precipitates. The precipitates were recovered by filtration and recrystallized from isopropyl alcohol to provide 1.0 g. of the hydrochloride of 4-(3-cyclohexylamino-2-hydroxypropoxy)indene. M.P. 168°–169° C.

| Elementary analysis as $C_{18}H_{26}NO_2Cl$: | | | | |
|---|---|---|---|---|
|  | C(%) | H(%) | N(%) | Cl(%) |
| Calculated: | 66.76 | 8.09 | 4.32 | 10.95 |
| Found: | 66.97 | 8.42 | 4.46 | 11.04 |

EXAMPLE VII

To a solution of 1 g. of 4-(2,3-epoxypropoxy)indene in 6 ml. of absolute ethanol was added 1.2 g. of tert-butylamine and the resulting solution was stirred at room temperature overnight. The resulting solution was concentrated under reduced pressure to give a yellow oily product, which was subjected to column chromatography using a column (having an inside diameter of 3.5 cm. and a height of 8 cm.) packed with silica gel. The 9th to 14th fractions (volume of one fraction is 10 ml.) recovered from the chromatographic column using acetone as the effluent were combined together and concentrated, and thereafter allowed to stand to form precipitates. The precipitates were recrystallized from n-hexane to provide 0.2 g. of white crystals of 4-(3-tert-butylamino-2-hydroxypropoxy)indene. M.P. 84°–85° C.

| Elementary analysis as $C_{16}H_{23}NO_2$: | | | |
|---|---|---|---|
|  | C(%) | H(%) | N(%) |
| Calculated: | 73.53 | 8.87 | 5.36 |
| Found: | 73.66 | 9.13 | 5.32 |

EXAMPLE VIII

To 5 ml. of isopropyl alcohol were added 0.4 g. of 4-(2,3-epoxypropoxy) indene and 0.8 g. of β-phenylisopropylamine. After heating the resulting solution at 50°–60° C. for 3 hours, isopropyl alcohol was distilled off at the same temperature under reduced pressure, and by further heating, excess β-phenylisopropylamine was distilled off. The residue thus obtained was dissolved in 30 ml. of n-hexane under heating, the insoluble materials were filtered and the filtrate thus obtained was concentrated to obtain oily materials. The oily materials were dissolved, in a small quantity of methanol and to the resulting material was added 10% hydrochloric acid to provide 0.5 g. of 4-(3-β-phenylisopropylamino-2-hydroxypropoxy)indene hydrochloride. M.P. 203°–205° C. (from methanol).

| Elementary analysis as $C_{21}H_{26}NO_2Cl$: | | | |
|---|---|---|---|
|  | C(%) | H(%) | N(%) |
| Calculated: | 70.08 | 7.28 | 3.89 |
| Found: | 70.19 | 7.19 | 4.14 |

EXAMPLE IX

Optical resolution of (±)-4-(3-isopropylamino-2-hydroxypropoxy)indene:

(a) (−)-4-(3-isopropylamino-2-hydroxypropoxy)indene 4.9 g. of (±)-4-(3-isopropylamino-2-hydroxypropoxy)indene and 7.5 g. of (−)-o,o-dibenzoyltartaric acid were dissolved in the mixture of 40 ml. of methanol and 20 ml. of water at 40°–50° C., and the resulting solution was cooled gradually to room temperature to form 6 g. of precipitates. The precipitates were recovered by filtration and recrystallized from 66% methanol [methanol:water = 2:1 (volume)], until the rotation of crystals became constant. 0.6 g. of (−)-4-(3-isopropylamino-2-hydroxypropoxy)indene (−)-o,o-dibenzoyltartarate was obtained $[\alpha]_D^{21} = -78.8$ (c=1.0, ethanol).

To 0.4 g. of (−)-4-(3-isopropylamino-2-hydroxypropoxy)indene(−)-o,o-dibenzoyltartarate were added 10 ml of 1 N hydrochloric acid and 20 ml of ether while stirring, and the water layer was separated and washed with ether. The water layer was neutralized with 10 ml of 1 N sodium hydroxide and extracted with 30 ml of n-hexane. After the n-hexane extract was dried over anhydrous sodium carbonate, the n-hexane was distilled off to provide 140 mg. of (−)-4-(3-isopropylamino-2-hydroxypropoxy)indene. $[\alpha]_D^{21} = -9.3$ (c=2.0, ethanol).

Hydrogen chloride was bubbled into the solution of 120 mg. of (−)-4-(3-isopropylamino-2-hydroxypropoxy)indene in ether to give 110 mg. of the hydrochloride of (−)-4-(3-isopropylamino-2-hydroxypropoxy)indene. The compound thus obtained was recrystallized from methanol-ether $[\alpha]_D^{21} = -25.2$ (c=2.0, ethanol).

(b) (+)-4-(3-isopropylamino-2-hydroxypropoxy)indene

The filtrate obtained according to a above was concentrated under reduced pressure to provide an oily residue. When the oily residue is used in place of (−)-4-(3-isopropylamino-2-hydroxypropoxy)indene(−)-o,o-dibenzoyltartarate in the procedure of a, 1.2 g. of (+)-4-(3-isopropylamino-2-hydroxypropoxy)indene were obtained. $[\alpha]_D^{21} = +6.2$ (c=1.0, ethanol).

To the solution of 1.2 g. of (+)-4-(3-isopropylamino-2-hydroxypropoxy)indene in 20 ml. of ether was added 10 ml. of ether containing 1.8 g. of (−)-o,o-dibenzoyltartaric acid to form an oily substance. The oily substance was recovered by filtration, and recrystallized from methanol, until the rotation of crystals became constant. 0.5 g. of (+)-4-(3-isopropylamino-2-hydroxypropoxy)indene 1/2(−)-o,o-dibenzoyltartarate was obtained. $[\alpha]_D^{21} = -36.8$ (c=1, 96% ethanol).

150 mg. of (+)-4-(3-isopropylamino-2-hydroxypropoxy)indene $\{[\alpha]_D^{21} = +8.8$ (c=1, ethanol)$\}$ and 110 mg. of the hydrochloride of (+)-4-(3-isopropylamino-2-hydroxypropoxy)indene $\{[\alpha]_D^{21} =$ +24.1 (c=1, ethanol)} were prepared by the method described in *a* by using (+)-4-(3-isopropylamino-2-hydroxypropoxy)indene.

What is claimed is:

1. A method of establishing an adrenergic β-receptor blockade which comprises administering to a patient in which such blockade is desired a pharmaceutically effective amount of a compound selected from the group consisting of 4-(3-isopropylamino-2-hydroxypropoxy)indene, 4-(3-tert-butylamino-2-hydroxypropoxy)indene and a non-toxic acid addition salt thereof.

2. A method according to claim 1, wherein the compound is 4-(3-isopropylamino-2-hydroxypropoxy)indene.

3. A method according to claim 1, wherein the compound is 4-(3-tert-butylamino-2-hydroxypropoxy)indene.

4. A compound selected from the group consisting of 4-(3-tert-butylamino-2-hydroxypropoxy)indene and a non-toxic acid addition salt thereof.

5. A pharmaceutical composition which comprises, as active ingredient, a compound selected from the group consisting of 4-(3-isopropylamino-2-hydroxypropoxy)indene, 4-(3-tert-butylamino-2-hydroxypropoxy)indene and a non-toxic acid addition salt thereof, and a pharmaceutically acceptable carrier therefor.

6. A composition as claimed in claim 5, wherein the active ingredient is 4-(3-isopropylamino-2-hydroxypropoxy)indene.

7. A composition as claimed in claim 5, wherein the active ingredient is 4-(3-tert-butylamino-2-hydroxypropoxy)indene.

* * * * *